(12) United States Patent
Kandori et al.

(10) Patent No.: US 7,340,289 B2
(45) Date of Patent: Mar. 4, 2008

(54) BIOMAGNETIC FIELD MEASURING APPARATUS

(75) Inventors: Akihiko Kandori, Kokubunji (JP); Tsuyoshi Miyashita, Fuchu (JP); Keiji Tsukada, Kashiwa (JP); Masahiro Murakami, Hitachinaka (JP); Kuniomi Ogata, Hachioji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 896 days.

(21) Appl. No.: 10/634,772

(22) Filed: Aug. 6, 2003

(65) Prior Publication Data

US 2004/0034299 A1     Feb. 19, 2004

(30) Foreign Application Priority Data

Aug. 7, 2002    (JP) ............................. 2002-229397

(51) Int. Cl.
   *A61B 5/05* (2006.01)
(52) U.S. Cl. ........................ 600/409; 600/511
(58) Field of Classification Search ................ 600/409, 600/425, 508, 511, 524
   See application file for complete search history.

(56) References Cited

U.S. PATENT DOCUMENTS

| | | | | |
|---|---|---|---|---|
| 5,372,139 A | * | 12/1994 | Holls et al. | .................. 600/511 |
| 5,666,959 A | * | 9/1997 | Deans et al. | ................. 600/511 |
| 6,269,262 B1 | * | 7/2001 | Kandori et al. | ............. 600/409 |
| 6,751,498 B1 | * | 6/2004 | Greenberg et al. | .......... 600/511 |
| 2004/0260169 A1 | * | 12/2004 | Sternnickel | ................. 600/409 |

FOREIGN PATENT DOCUMENTS

| | | |
|---|---|---|
| JP | 63-099840 | 5/1988 |
| JP | 6-237909 | 8/1994 |
| JP | 10-211180 | 8/1998 |
| JP | 11-197128 | 7/1999 |
| JP | 11-318842 | 11/1999 |
| JP | 2001-029320 | 2/2001 |

OTHER PUBLICATIONS

American Journal of Obstetrics & Gynecology, vol. 125, No. 8, Aug. 15, 1976, pp. 1115-1120.
Physiol. Meas., vol. 16, 1995, pp. 49-54.

* cited by examiner

*Primary Examiner*—Brian L. Casler
*Assistant Examiner*—Jacqueline Cheng
(74) *Attorney, Agent, or Firm*—Mattingly, Stanger, Malur & Brundidge, P.C.

(57) ABSTRACT

A biomagnetic field measuring apparatus for performing (1) processes for removing a magnetic field waveform generated by a maternal heart from a waveform of a biomagnetic field measured, (2) processes for obtaining a template waveform of a magnetic field waveform generated by the fetal heart from a waveform, from which the magnetic field waveform generated by the maternal heart has been removed, (3) processes for obtaining a waveform of a cross correlation coefficient between the waveform, from which the magnetic field waveform generated by the mother's hears was removed, and the template waveform, and (4) a process for detecting peaks from a waveform of the cross correlation coefficient, and displaying times of appearance of the detected peaks on a display unit.

6 Claims, 11 Drawing Sheets

HEART'S MAGNETIC FIELD SIGNAL WAVEFORM (OF MOTHER AND FETUS)

ELECTROCARDIOGRAPHIC WAVEFORM (MOTHER BODY)

⇩ MOTHER-BODY SIGNAL REMOVAL PROCESS

⇩ FETUS'S QRS WAVE REMOVAL PROCESS

BIOMAGNETIC FIELD MEASURING APPARATUS

BACKGROUND OF THE INVENTION

The present invention relates generally to a biomagnetic field apparatus using SQUID (Super-conducting Quantum Interference Device hereafter referred to as SQUID) magnetometers for measuring minute magnetic fields generated from the heart, the brain or the like of an adult, a child, an unborn baby or a fetus or the like. Particularly, the invention relates to an apparatus for extracting a fetal heart beats from waveforms of a measured magnetocardiographic signal of the fetus.

Heretofore, a biomagnetic field measuring apparatus employing SQUID magnetometers has been used in measurement of a minute biomagnetic field (a measured magnetic field is called a cardiac magnetic field (magnetocardiogram) or a brain magnetic field (magnetoencephalogram)) which is formed by an ion current generated concurrently with the myocardial electric activity within a subject (muscular activity in general) or the neuron activity in the brain. The motion of an ion current reflects the electric activity of the subject. By utilizing the motion of an ion current, useful information can be obtained and many researches are being carried out. There have been reports on observations of the automatic nerve activity by obtaining RR-intervals of a fetal heart beats from measured magnetic fields by performing Fast Fourier Transform analysis (FFT analysis), and the clinical effectiveness of analysis of the fetal RR interval has been considered.

Heretofore, normally, when detecting R-wave peaks a certain threshold value was set in advance, and peaks that were higher than this threshold value were detected. (Prior Art 1: Am. J. Obstet. Gynecol., 125, pp. 1115-1120, 1976) Also, there is a report on a case where an autocorrelation method was applied which used an electrocardiographic signal from a fetus. (Prior Art 2: Physiol. Meas., 16, pp. 49-54, 1995)

On the other hand, in the sector of electrocardiography, an apparatus structure has been reported, which collects templates of waveforms considered representing the state of the heart of an examined subject, extracts only necessary data for precise diagnosis of the state associable with the templates from the collected waveforms by using a data-compression algorithm, forms a template waveform for a reduced-data electrocardiographic waveform template by using extracted data, then correlates the reduced-data electrocardiographic waveform template with electro-cardiographic waveforms of the patient, and gives a diagnosis from a correlation result. (Prior Art 3: JP-A-10-211180)

In the prior art 1, since magnetocardiographic waveforms of a fetus are of a very weak signal with only a few of pT at each R-wave peak, if there is a baseline drift with the low frequency due to the mother's breathing, for example, it is impossible to set a threshold value, making it difficult to detect the R waves with a better detection rate. In the prior art 2, there is no description of a method, for example, of detecting R waves with high sensitivity. Further, in the prior art 3, there is no description of a technique for extracting the times of peak occurrence in waveforms from correlation results. Just as described, in the prior art, there has been no means for automatic detection of R waves with a high detection rate, which can perform R-R distance analysis of fetuses. For this reason, no means of detecting R waves has been available to many researchers other than visual detection, and a fairly long time has been taken for R-R analysis of fetuses.

The present invention has as its object to provide a biomagnetic field measuring apparatus capable of accurately detecting the peak times in waveforms (P waves, QRS waves, T waves, etc.) with high precision and stability by the electric activity of a fetal heart from minute magnetic field waveforms produced by the fetal heart.

SUMMARY OF THE INVENTION

In the following description, a "mother's body signal" represents magnetic field waveforms generated by the mother's heart, and a "fetal signal" represents magnetic field waveforms generated by a fetal heart, a "template waveform of a mother's body signal" represents waveforms of a mother's body signal each with a predetermined time width, during which a time of the mother's heart beat is set as the central time, the times of the mother's heart beat being obtained by detecting the peaks of a QRS wave, a p wave, a T wave, or the like, which are higher than a predetermined threshold value, from the mother's electrocardiographic waveforms used as reference signal, a "raw waveforms of a fetal signal" represents magnetic field waveforms (raw data) collected by measurement exclusive of template waveforms of the maternal signal, a "template waveform of a fetal signal" represents waveforms of a fetal signal each with a predetermined time width which has a peak time as the central time, the peak times being obtained by detecting peaks of a QRS wave, a P wave, a T wave, or the like, higher than a predetermined threshold value, from raw waveforms of the fetal signal.

In a biomagnetic field measuring apparatus according to the present invention, a single unit or a plurality of units of SQUID magnetometers incorporating superconducting quantum interference devices are used to measure a magnetic field generated by the subject under examination, remove magnetic field waveforms generated by a mother's body (a maternal signal) from measured biomagnetic field waveforms of the subject to obtain magnetic field waveforms generated by the fetal heart, generate a template waveform of the fetal signal, obtain waveforms of a cross correlation coefficient between the waveforms of the fetal signal and the template waveform, and detect peaks of the cross correlation coefficient, and display times at which the detected peaks occurred.

According to a biomagnetic field measuring apparatus in the present invention, even with minute magnetic field waveforms generated by a fetal heart, such as one whose baseline drifts, it is possible to obtain with stability and high sensitivity the peaks of waveforms of a P wave, a QRS wave, T wave, or the like produced by the electric activity of a fetal heart.

Other objects, features and advantages of the invention will become apparent from the following description of the embodiments of the invention taken in conjunction with the accompanying drawings.

DESCRIPTION OF THE EMBODIMENTS

A biomagnetic field measuring apparatus successively performs (1) a computing process for removing magnetic field waveforms generated by a mother's heart from measured biomagnetic field waveforms of the subject, (2) a computing process for obtaining a first template waveform of magnetic waveforms generated by a fetal heart from waveforms exclusive of magnetic field waveforms generated by the mother's heart, (3) a computing process for obtaining waveforms of a cross correlation coefficient between waveforms exclusive of magnetic field waveforms generated by the mother's heart and the first template waveform, and (4) a computing process for detecting peaks from waveforms of the cross correlation coefficient, and then the apparatus displays times at which the detected peaks occurred. The process (1) includes a computing process for obtaining a second template waveform of magnetic field waveforms generated by the mother's heart, a baseline correcting process for zeroing the initial point and the end point of the second template waveform, and a computing process for removing the second template waveform subjected to the baseline correcting process from the measured biomagnetic field waveforms of the subject. The process (1) is executed by using as a reference signal the mother's electrocardiographic waveforms measured simultaneously with the detection of biomagnetic field waveforms of the subject. The first and the second template waveforms can be obtained by a sum-averaging process. The process (3), which uses a plurality of SQUID magnetometers (multi-channel), includes a process for obtaining waveforms of a cross correlation coefficient from the subject's biomagnetic field waveforms measured by each SQUID magnetometer (each channel), and a process for obtaining an average waveform of the waveforms of cross correlation coefficients obtained by the plurality of channels, and an average waveform is used as waveform of cross correlation coefficients.

Preferred embodiments of the present invention will be described with reference to the accompanying drawings.

Figure 1:
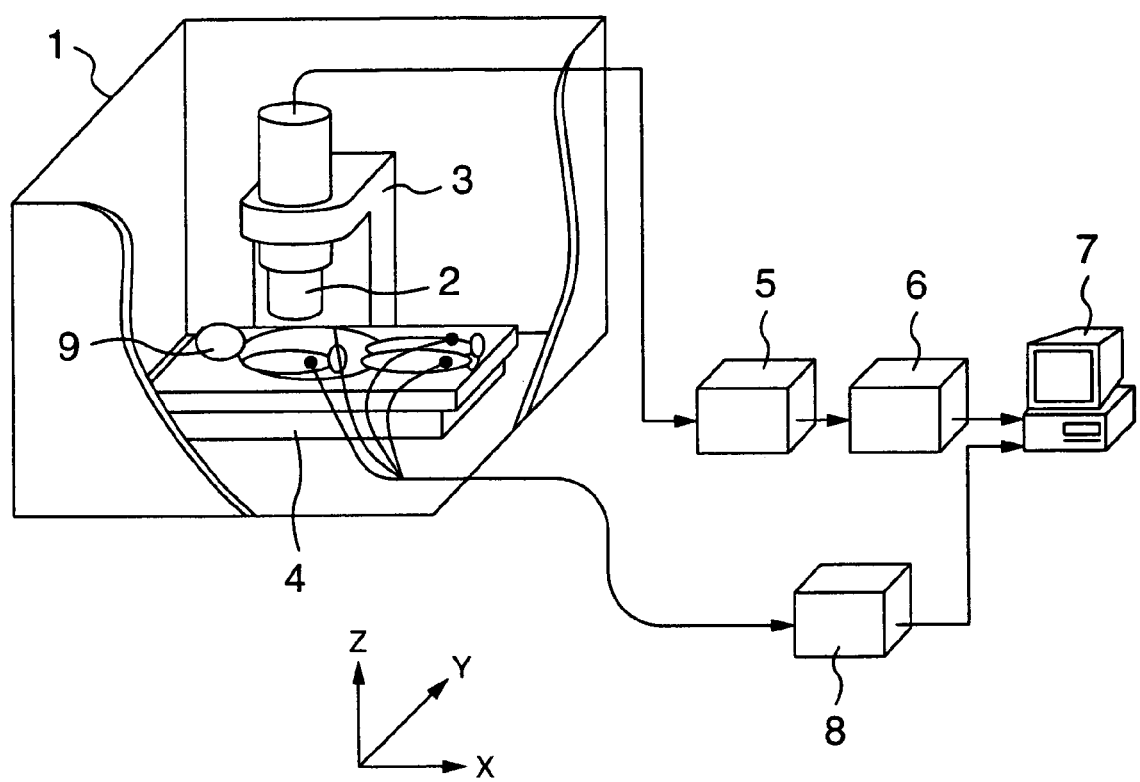
FIG. 1 is a diagram showing a structural example of a biomagnetic field measuring apparatus according to an embodiment of the present invention.

FIG. 1 is a diagram showing a structural example of a biomagnetic field measuring apparatus of the present invention. As shown in FIG. 1, in a magnetic shield room 1 to shield external magnetic fields, there are provided a bed 4 on which a subject 9 lies, a cryostat 2 for containing a plurality of SQUID magnetometers (multi-channel) and a coolant (liquid helium or liquid nitrogen) to keep the SQUID magnetometers in superconducting state, and a gantry 3 for mechanically holding the cryostat 2. The bed 4 is movable in the X-, Y- and Z-directions. Arranged external to the magnetic shield room 1 are a drive circuit 5 for the SQUID magnetometers, an amplifier-circuit and filter-circuit unit 6, a data-accept and data-analysis computer (arithmetic processor) 7, and a circuit 8 for receiving external input signals from cardiography equipment, for example.

A biomagnetic field signal detected by the SQUID magnetometers is amplified by the amplifier-circuit and filter-circuit unit 6, and undergoes signal processes, such as a low-pass filter to pass low-frequency signals lower than a set frequency, a high-pass filter to pass high-frequency signals higher than a set frequency, or a notch filter to stop only commercial power frequencies. After this, the biomagnetic field signal is accepted as raw data into a personal computer 7. signal waveforms from the circuit 8 for receiving external input signals from a electrocardiographic monitor, for example, are sent as raw data into the personal computer 7. The personal computer 7 can also store received raw data in a raw data file, display waveforms on the screen, or carry out a waveform signal process or an isomagnetic chart process and display process results.

Figure 2:
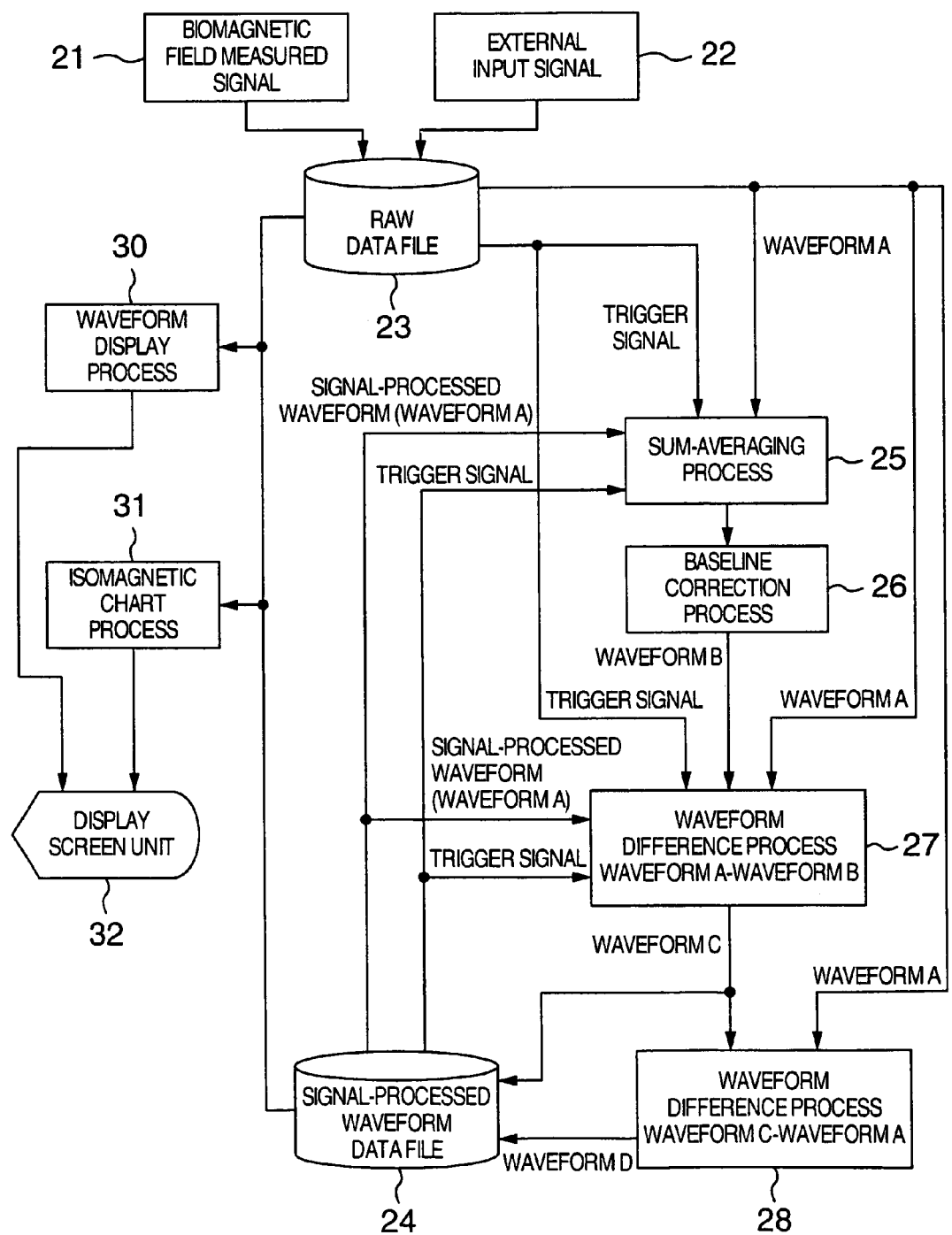
FIG. 2 is a flow diagram showing a concept of data process according an embodiment of the present invention.

FIG. 2 is a flow diagram showing a concept of data process according to an embodiment of the present invention. In FIG. 2, a biomagnetic field measurement signal 21 and an external input signal 22 captured in the personal computer 7 in FIG. 1 are stored in a raw data filer 23. Besides storage in the raw data file 23, a biomagnetic field measurement signal 21 and an external input signal 22 can be subjected to signal processes such as a sum-averaging process 25 conducted in real time by a DSP (Digital Signal Processor), not shown. More specifically, a file, data of which is processed, is called from the raw data file 23, and out of signal waveform data of the called file, waveforms of a channel of either magnetic signal waveforms or input signal waveforms of some device other than the magnetometers are used as a trigger signal, and by using this trigger signal, a sum-averaging process 25 is carried out on the biomagnetic field measurement signal 21 (waveform A).

Then, a baseline correcting process 26 is performed on a waveform obtained by the sum-averaging process 25. After this, by using the trigger signal, the waveform obtained by the baseline correcting process 26 (waveform B) is sent to a differentiation process 27 between waveform A and waveform B to obtain waveform C which is to be stored in a signal-processed waveform data file 24. By a differentiation process 28 between waveform C and waveform A, waveform D is obtained. The waveform D is stored in a signal-processed waveform data file 24.

Data in the signal-processed data file 24 can be repeatedly subjected to a series of data processing steps: the sum-averaging process 25, the baseline correcting process 26, differentiation process 27, and the differentiation process 28. Further, data in the signal-processed data file 24 may be used as a trigger signal. Waveform data in the raw data file 23 or the signal-processed waveform data file 24 is subjected to a waveform display process 30 and an isomagnetic chart depending on input setting, such as a display range, a display scale, a waveform channel to be displayed, or the like, and results are displayed on the display screen 32.

Figure 3:
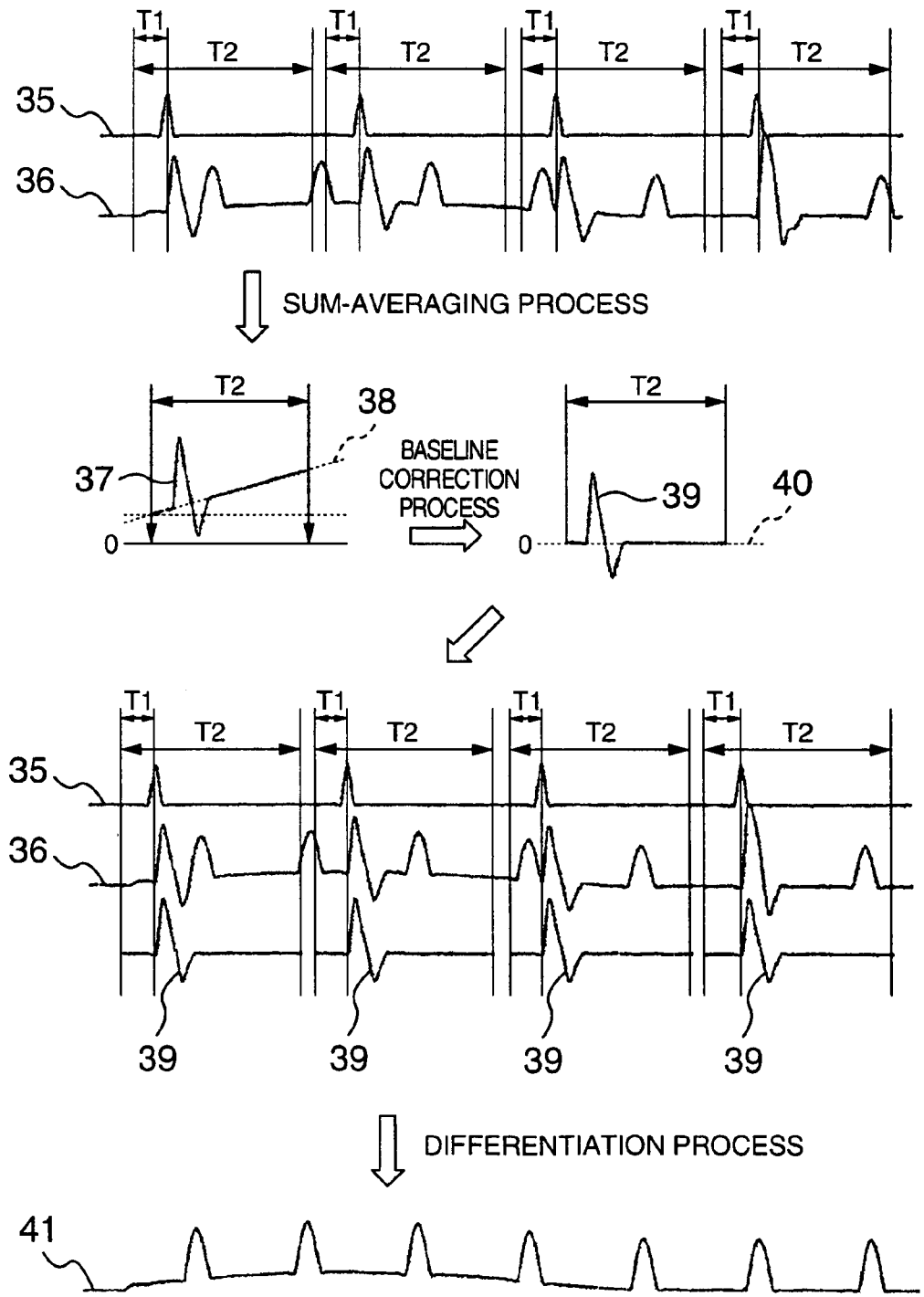
FIG. 3 is a diagram showing a concept of a signal processing method for a sum-averaging process, a baseline correcting process, and a waveform differentiation process according to an embodiment of the present invention.

FIG. 3 is a diagram showing a concept of a signal processing method of the sum-averaging process 25, the baseline correcting process 26, and the waveform differentiation process 27 according to an embodiment of the present invention. In FIG. 3, as an embodiment, a case will be described which had as its object to measure a magnetic field signal of a fetus. In response to a mother's electrocardiographic waveforms 35 as a trigger signal, the waveforms 36 of a magnetic field signal measured from the fetus's mother's abdomen are subjected to a sum-averaging process at each addition section for a duration of T2 sec. which is to start T1 sec. before the time of a peak value of the trigger signal. Generally, from a mother's electrocardiographic waveforms, the fetal electrocardiographic waveforms can hardly be detected or even if they are detected, they are very small and low. Therefore, when a threshold value is set for waveforms from cardiographic equipment and those waveforms undergo a peak value detection, only the peak values of mother's electrocardiographic waveforms are detected. By using peak values as a trigger signal, a sum-averaging process is carried out at each addition section T2 to obtain waveforms 37. By the sum-averaging process, the magnetic field signal waveforms of the fetal heart not synchronous with the mother's electrocardiographic waveforms 35 attenuate, so that it is possible to extract sum-averaged waveforms 37 of the maternal heart's magnetic field signal synchronous with the electrocardiographic waveforms 35. Note that the waveforms discussed in this document, such as the waveforms 35 in FIG. 3, are waveforms that occur successively in a train fashion in one signal.

The values of signal strength at different times at two optional points of each waveform 37 are connected with a straight line, and this straight line is set as a baseline 38 of the waveform 37. The magnetic field signal waveforms 36 measured at the mother's abdomen sometimes include drifts of waveforms caused by the mother's breathing vibration, and in some cases, the drifts of waveforms cannot be removed completely only by the sum-averaging process. As a result, as shown in the waveform 37, the waveform comes to have an inclined baseline 38 and an offset. By executing a baseline correcting process to make the baseline 38 like the baseline 40 without any gradient, and by performing the baseline correcting process in a manner to eliminate the offset value, the waveforms 39 can be obtained. The execution of the baseline correcting process provides an effect that the joining portions between waveforms at different sections are smoothed when a differentiation process is performed, which will be described in the following.

If, timed with electrocardiographic signal waveforms 35 (trigger signal), the differentiation process is carried out between the magnetic field signal waveforms 36 measured from the mother's abdomen and the baseline-corrected waveforms 39 of the maternal heart's magnetic field signal, the differentiation-processed waveforms 41 of the fetal heart's magnetic field signal as target data were obtained. Further, when the differentiation process is performed between the waveforms 36 and the waveforms 41, the maternal heart's long-time magnetic signal waveforms (not shown) can be obtained. In the above-mentioned processes, the processes can be made simpler if an external input signal, such as one from a cardiographic device, were used. Even without an external input signal, similar effects can be achieved by processing the signal waveforms from the magnetometers in accordance with the base time.

Figure 4:
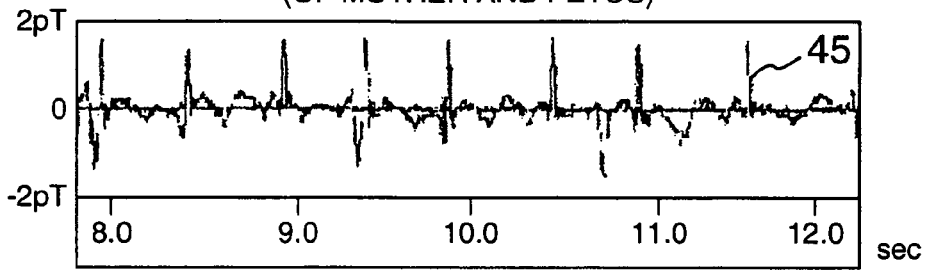
FIG. 4 is a diagram showing a clinical case of signal processing according to an embodiment of the present invention.
Figure 4:
Figure 4:
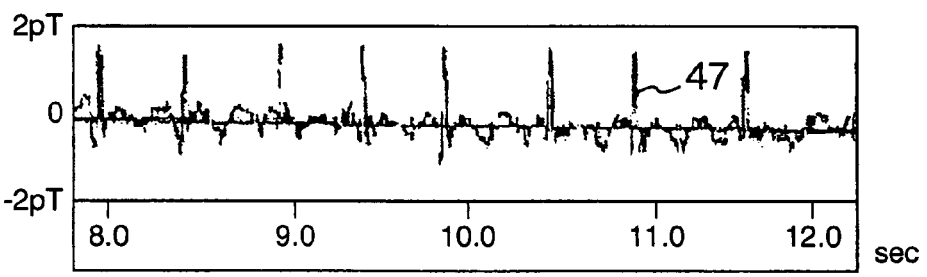
Figure 4:
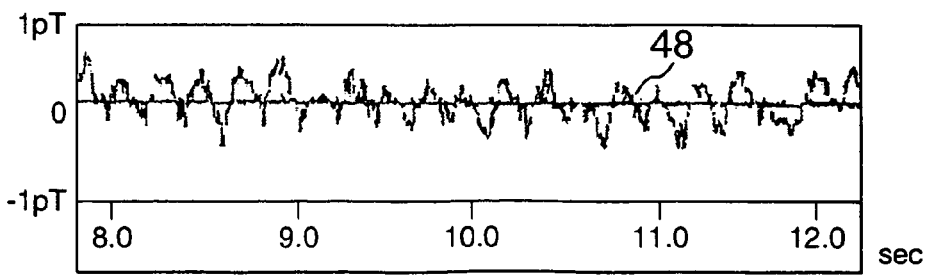

FIG. 4 is a diagram showing a clinical case of signal process according to an embodiment of the present invention. To take an example, in order to measure the fetal heart's magnetic field signal, the magnetic field signal waveforms 45 was measured at the mother's abdomen (collected data), and the waveforms 45 have both the magnetic field signal waveforms generated by the fetal heart and the magnetic field signal waveforms generated by the mother's heart superposed in it. In response to externally-input electrocardio-graphic waveforms 46 from the mother's body used as a trigger signal, waveforms (used as reference data) are obtained by subjecting the magnetic field waveforms 45 initially to the sum-averaging process 25 (FIG. 2) and subsequently to the baseline correcting process 26 (FIG. 2). When the obtained waveforms (reference data) are further subjected to the waveform difference process 27 (FIG. 2) between the obtained waveforms and the magnetic field signal waveforms 45, the mother's heart's magnetic field signal is removed, so that the target waveforms 47 are obtained. The waveforms 47 are the fetal heart's magnetic field signal waveforms. To remove QRS waveforms from the fetal heart's waveforms, by using recurring peaks of R waves of the waveforms 47 as the trigger signal, the waveforms 47 are again subjected to the sum-averaging process 25 (FIG. 2) and the baseline correcting process 26 (FIG. 2), and when obtained waveforms (reference data) are subjected to the waveform differentiation process 27 (FIG. 2) between the obtained waveforms and the magnetic field signal waveforms 47, waveforms 48 exclusive of the QRS waves of the fetal heart waveform can be extracted. This clinical case, in which there are waveforms 48 characterized by cyclical sawtoothed waveforms (called F waves), is diagnosed as atrial flutter.

Figure 5:
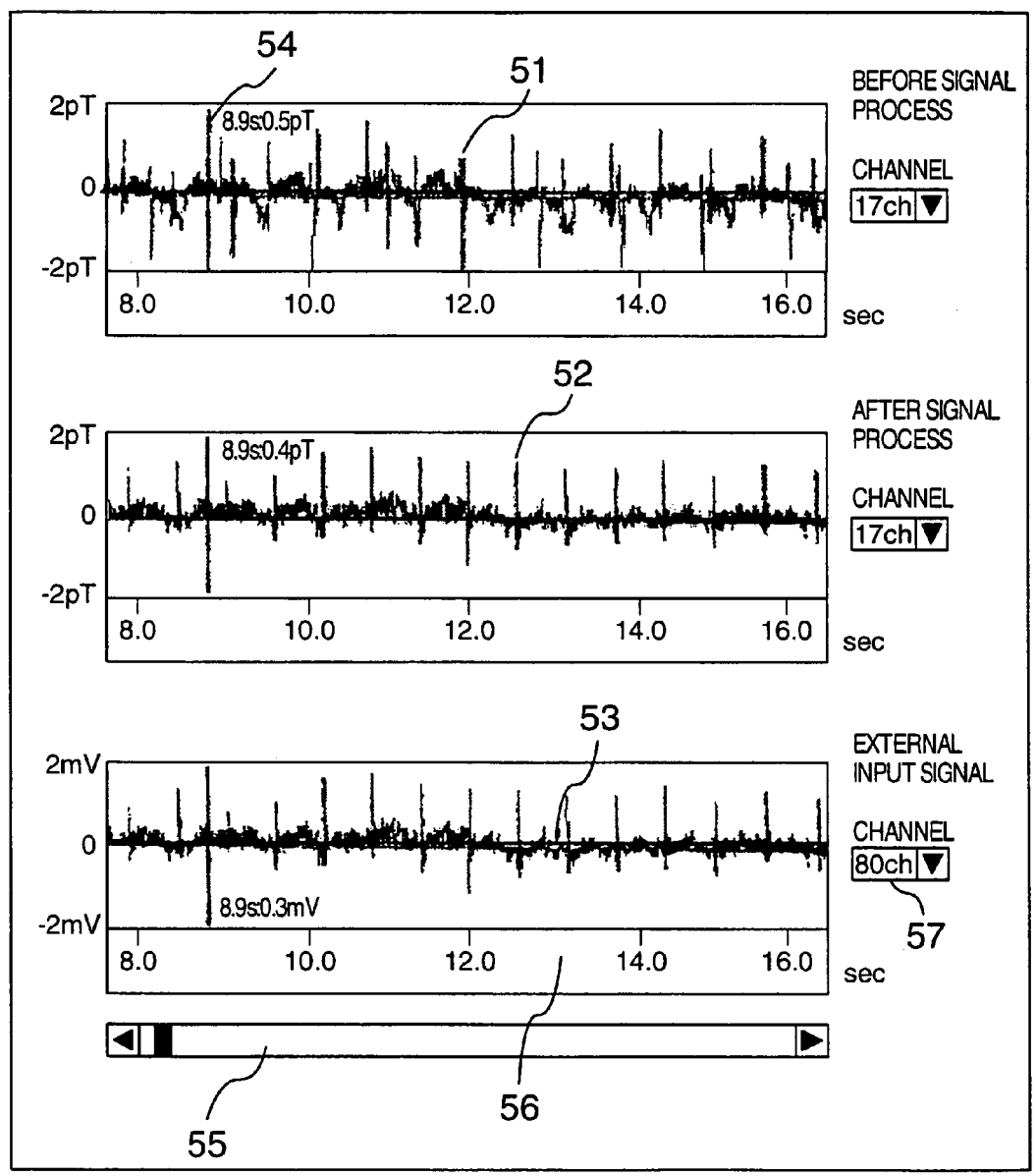
FIG. 5 is a diagram showing an example of a waveform display screen image according to an embodiment of the present invention.

FIG. 5 is a diagram showing an example of a waveform display screen image according to an embodiment of the present invention. In this data processing, the magnetic field signal waveforms 51 were measured from a mother's abdomen in order to measure a magnetic field signal generated by a fetal heart, the mother's electrocardiographic waveforms 53 were received as an external input signal, and the fetal heart magnetic field waveforms 52 were obtained by performing the sum-averaging process 25 (FIG. 2), the baseline correcting process 26 (FIG. 2), and the waveform differentiation process 27 (FIG. 2) on the magnetic field signal waveforms 51 by using the above-mentioned electrocardiographic waveforms 53 as the trigger signal. As shown in FIG. 5, those different series of waveforms are arranged to appear in the same display screen image and for the same time series, it is easy to visually compare the maternal signal with the fetal signal from a viewpoint of time-based relation.

By further performing the differentiation process between the magnetic field signal waveforms 51 and the fetal heart magnetic field signal waveforms 52, the maternal heart's magnetic field signal waveforms (not shown) can be extracted. In such a case, it is possible to add a waveform display window to also display the extracted maternal heart's magnetic field signal waveforms on the same display screen for the same time series. As for waveform display channels, clicking the ▼ button in the channel select box 57 opens a pull-down menu, from which a desired channel is selected. The time 56 for waveform display can be scrolled by using the scroll bar 55. In conjunction with this, the times for the waveforms 51 and the waveforms 52 are also scrolled. When the cursor 54 is moved, the signal strength and the time of waveforms are displayed at the position of the cursor 54. Note that as one cursor is moved, the cursors for other waveforms are also moved in an interlocked manner.

Figure 6:
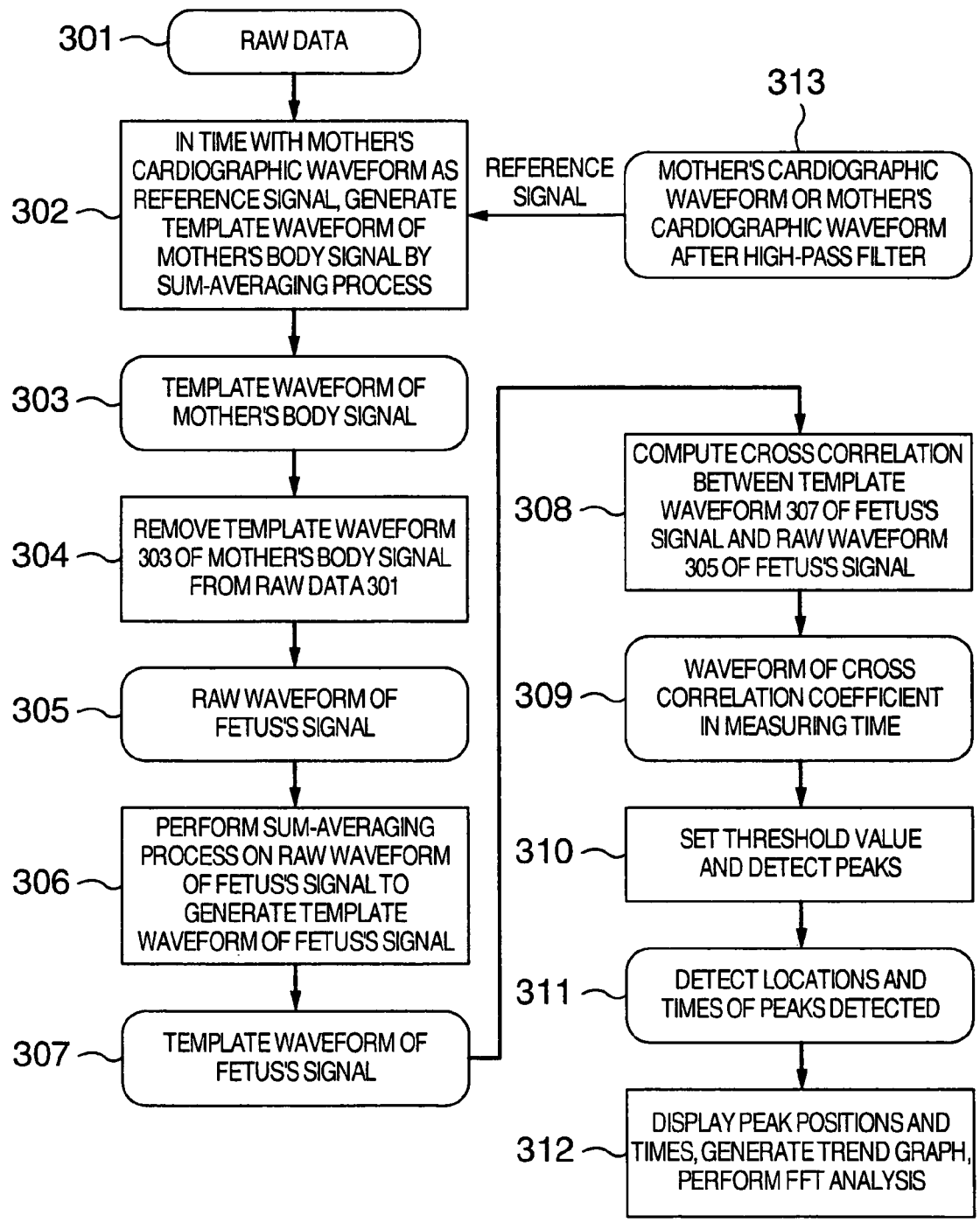
FIG. 6 is a flow diagram showing a peak detection procedure according to the present invention.

FIG. 6 is a flow diagram showing a procedure for detecting the peaks according to the present invention. By using the mother's electrocardiographic waveforms (or the mother's electrocardiographic waveforms after the high-pass filter) 313 as the reference signal, a template waveform 303 of the maternal signal (magnetic field waveform generated by the mother's heart) is formed from raw data 301 collected in the personal computer 7 in FIG. 1. From the mother's electrocardiographic waveforms 313 used as the reference signal, the times of the mother's heart beat are obtained by detecting the peaks of a QRS wave, a p wave, a T wave, or the like, which are higher than a predetermined threshold value.

By the sum-averaging process 25 (FIG. 2) of adding up the waveforms of a maternal signal for N heart beats at each channel, each waveform having a predetermined time width in which a time of the mother's heart beat is set as the central time thereof, and dividing the waveforms of the maternal signal after the adding-up step, by N, the template waveform 303 of a sum-averaged maternal signal with a better S/N ratio can be obtained. In order to zero the values of the initial point and the end point of the template waveform of the maternal signal, the baseline correcting process 26 (FIG. 2) is performed to null the gradient of the straight line connecting the initial point and the end point of each waveform. Details of those processes have already been described when reference was made to FIGS. 2 to 5.

By performing a process 304 to subtract the template waveform 303 of the maternal signal from raw data 301 collected by measurement, raw waveforms 305 of the fetal signal are generated. More specifically, by the process to subtract the template waveform 303 timed with the times of mother's heart beats in the raw data 301, raw waveforms of the fetal signal can be generated.

The raw waveforms 305 of the fetal signal are subjected to the sum-averaging process to generate the template waveform of the fetal signal. As in the process 302, in this sum-averaging process, by detecting the peaks of QRS waves, for example, of the fetal signal, which are higher than a specified threshold value, and adding up a number of waveforms for M heart beats to the waveforms of the fetal signal and then dividing the waveforms after the adding-up step, by M, a sum-averaged template waveform of the fetal signal with better S/N ratio can be obtained. If the template waveform 307 of the fetal signal is generated for each type of target waveform, such as QRS waves, P waves or T waves, the peak times of QRS waves, the peak times of P waves and the peak times of T waves can be detected independently.

Next, a process 308 is performed to compute a cross correlation coefficient between a template waveform 307 of the fetal signal and raw waveforms 305 of the fetal signal.

By the process 308, waveforms 309 of the cross correlation coefficient in a measuring time can be generated. By setting a threshold value in the waveforms 309 of the cross correlation coefficient in the measuring time, and performing a process 310 to detect peaks, times of peak occurrences can be detected 311. The personal computer 7 executes a process 312 to display the positions and the times of detected peaks, generate a trend graph and perform FFT analysis, and the computer 7 shows the times of detected peaks, trend graph, and FFT analysis results on the display screen.

Figure 7:
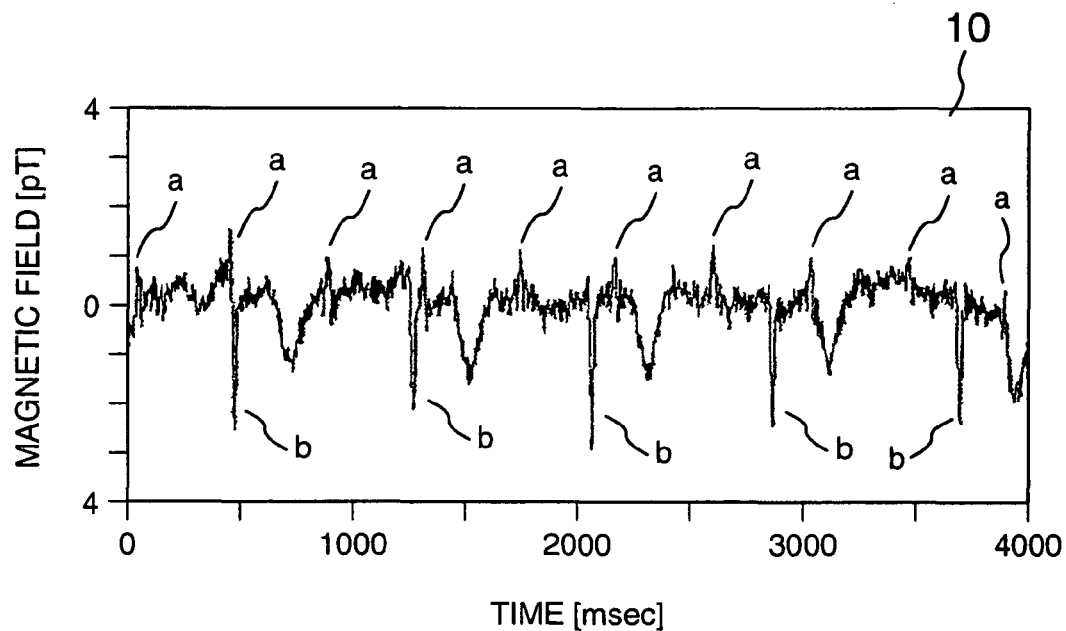
FIG. 7 is a diagram showing raw waveforms of the magnetocardiographic waveforms of a fetus according to an embodiment of the present invention.

FIG. 7 is a diagram showing raw waveforms 10 (301 in FIG. 6) for magnetocardiographic waveforms of a fetus according to an embodiment of the present invention. As shown in FIG. 7, in the raw waveforms 10, they appeared in a mixed form the magnetic field waveforms b generated by the mother's heart and the magnetic field waveforms a generated by the fetal heart. With a healthy fetus, the fetal heart beats twice faster than in an adult. Therefore, the magnetic field waveforms a generated by a fetal heart occur about twice as many as the magnetic field waveforms b generated by the maternal heart.

Figure 8:
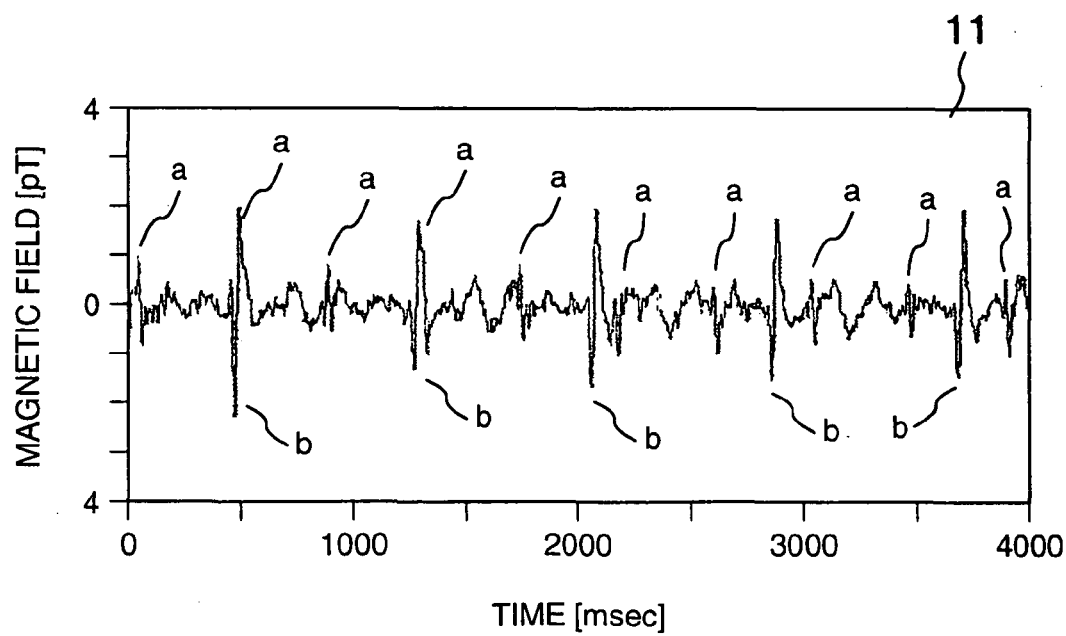
FIG. 8 is a diagram showing waveforms after a digital filtering process of a 5 Hz-50 Hz band-pass filter executed on raw waveforms in FIG. 7.

FIG. 8 is a diagram showing waveforms 11 after a digital filtering process of a 5 Hz-50 Hz band-pass filter executed on the raw waveforms 10 (301 in FIG. 6) in FIG. 7. The process by the band-pass filter is not necessarily required, and therefore it is not included in FIG. 6. The band-pass filter process serves to remove a large drifts of the baseline and small noise components lying on the baseline, making it possible to detect the peaks with higher precision.

Figure 9:
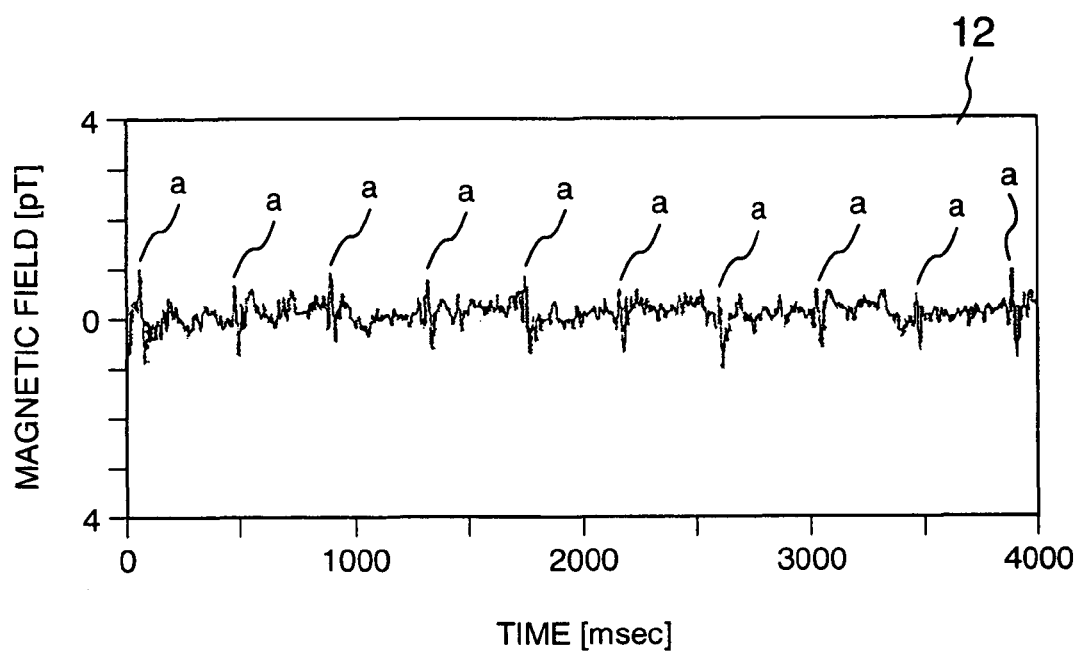
FIG. 9 is a diagram showing magnetic field waveforms generated by a fetal heart obtained by removing magnetic field generated by a mother's heart from the raw waveforms in FIG. 8.

FIG. 9 is a diagram showing magnetic field waveforms generated by the fetal heart, which are obtained by removing a magnetic field generated by the maternal heart from the raw waveforms in FIG. 8. FIG. 9 shows the fetus's raw waveforms 12 obtained by removing the template waveform of the maternal signal. The raw waveforms 12 can be generated by the process 304 to remove the template waveform 303 of the generated maternal signal from the raw waveforms 11 in FIG. 8 obtained by the band-pass filter process of the raw waveforms in FIG. 7 (corresponding to the process 301 in FIG. 6, though the high-pass filter process is performed).

Figure 10:
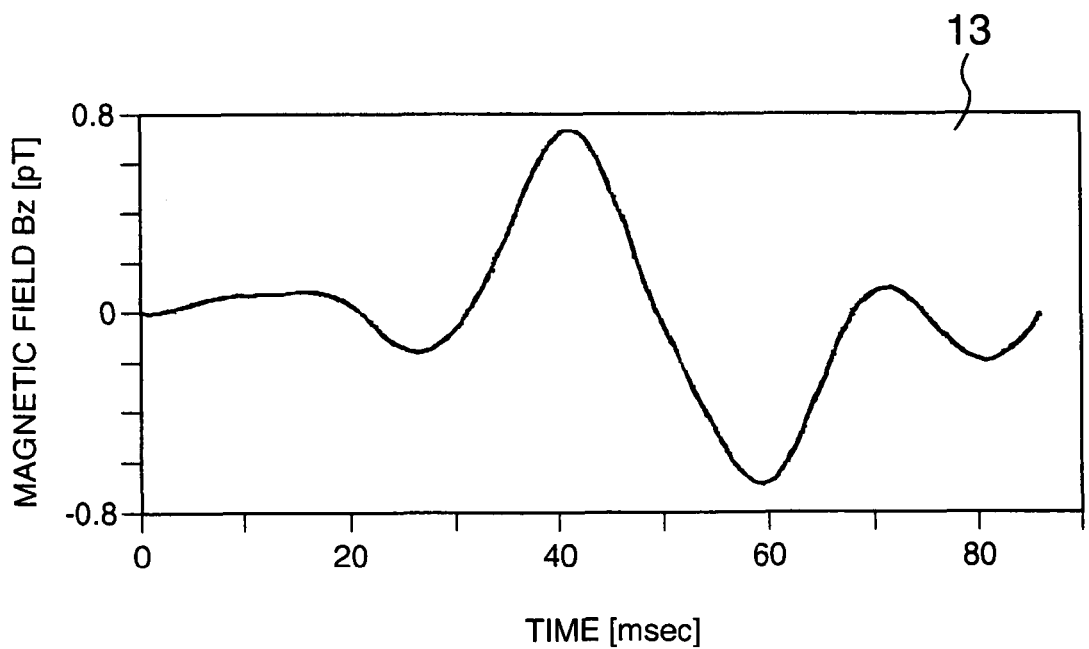
FIG. 10 is a diagram showing a sum-averaged waveform formed by a sum-averaging process synchronized with R waves from magnetic field waveforms generated by a fetal heart shown in FIG. 9.

FIG. 10 is a diagram showing a sum-averaged waveform (the template waveform 13 of the fetal signal) formed by an sum-averaging process synchronized with R waves from magnetic field waveforms generated by the fetal heart shown in FIG. 9. The waveform in FIG. 10 shows the result of generation of the template waveform 13 of the fetal signal (307 of FIG. 6) by detecting the peaks of QRS waves of the fetal signal, which are higher than a predetermined threshold value, adding up a number of waveforms for 100 heart beats, and dividing the waveforms after the adding-up step, by 100.

Figure 11:
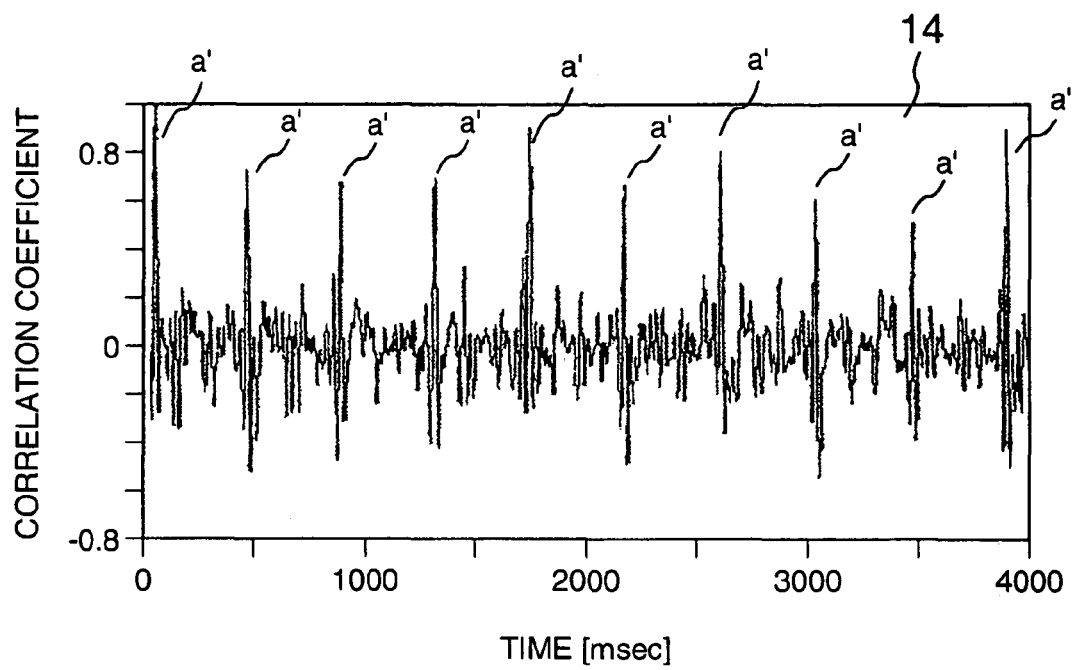
FIG. 11 is a diagram showing waveforms of cross correlation coefficient within a measuring time obtained by computing a cross coefficient between magnetic field waveforms generated by a fetal heart in FIG. 9 and the sum-averaged waveform in FIG. 10.

FIG. 11 is a diagram showing waveforms 14 of cross correlation coefficient within a measuring time, obtained by computing a cross correlation coefficient between the magnetic field waveforms 12 generated by the fetal heart in FIG. 9 and the sum-averaged waveform in FIG. 10 (the template waveform 13 of the fetal signal). It is understandable that in the waveforms 14 of cross correlation coefficient, waveforms a' of cross correlation coefficient, which are generated by the fetal heart are detected at times which correspond to times of R waves of the fetus. By setting a predetermined threshold value (0.8 for example) for the waveforms a' of the cross correlation coefficient and detecting the times at which the peaks occur, the peak times of R waves can be detected.

Figure 12:
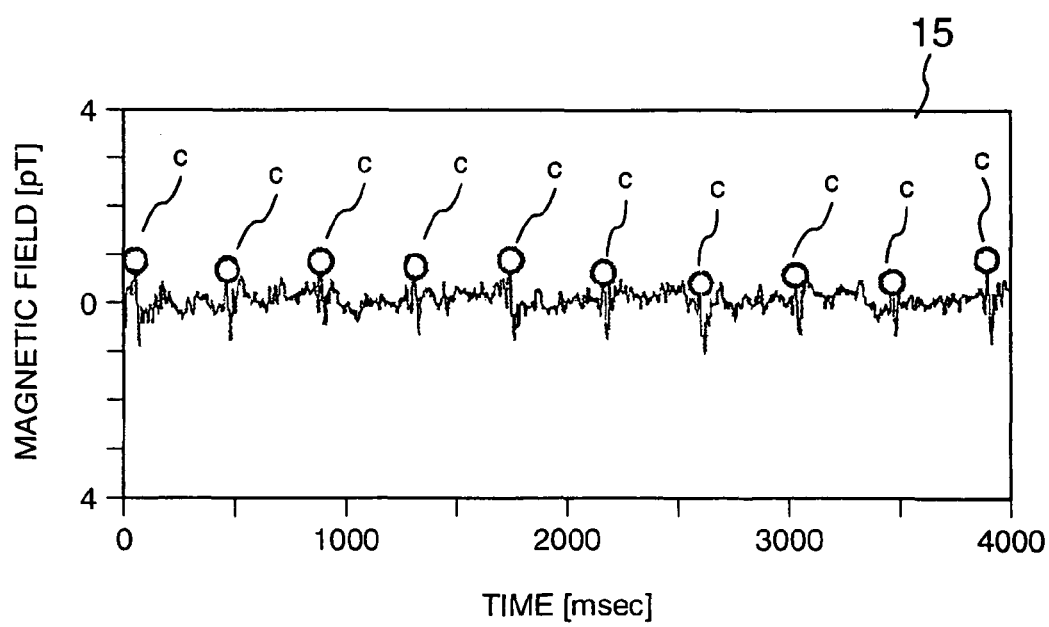
FIG. 12 is a diagram showing waveforms 15 which indicate the times when the peaks were detected from the waveforms of the cross correlation coefficient in FIG. 11 by putting round marks on the magnetic field waveforms generated by the fetal heart as shown in FIG. 9.

FIG. 12 is a diagram showing waveforms 15 which indicate the times when the peaks were detected from the waveforms of the cross correlation coefficient in FIG. 11 by putting round marks on the magnetic field waveforms 12 generated by the fetal heart as shown in FIG. 9. By checking the round marks on the waveforms 15 in FIG. 12, the reliability of the detected peaks can be evaluated.

Figure 13:
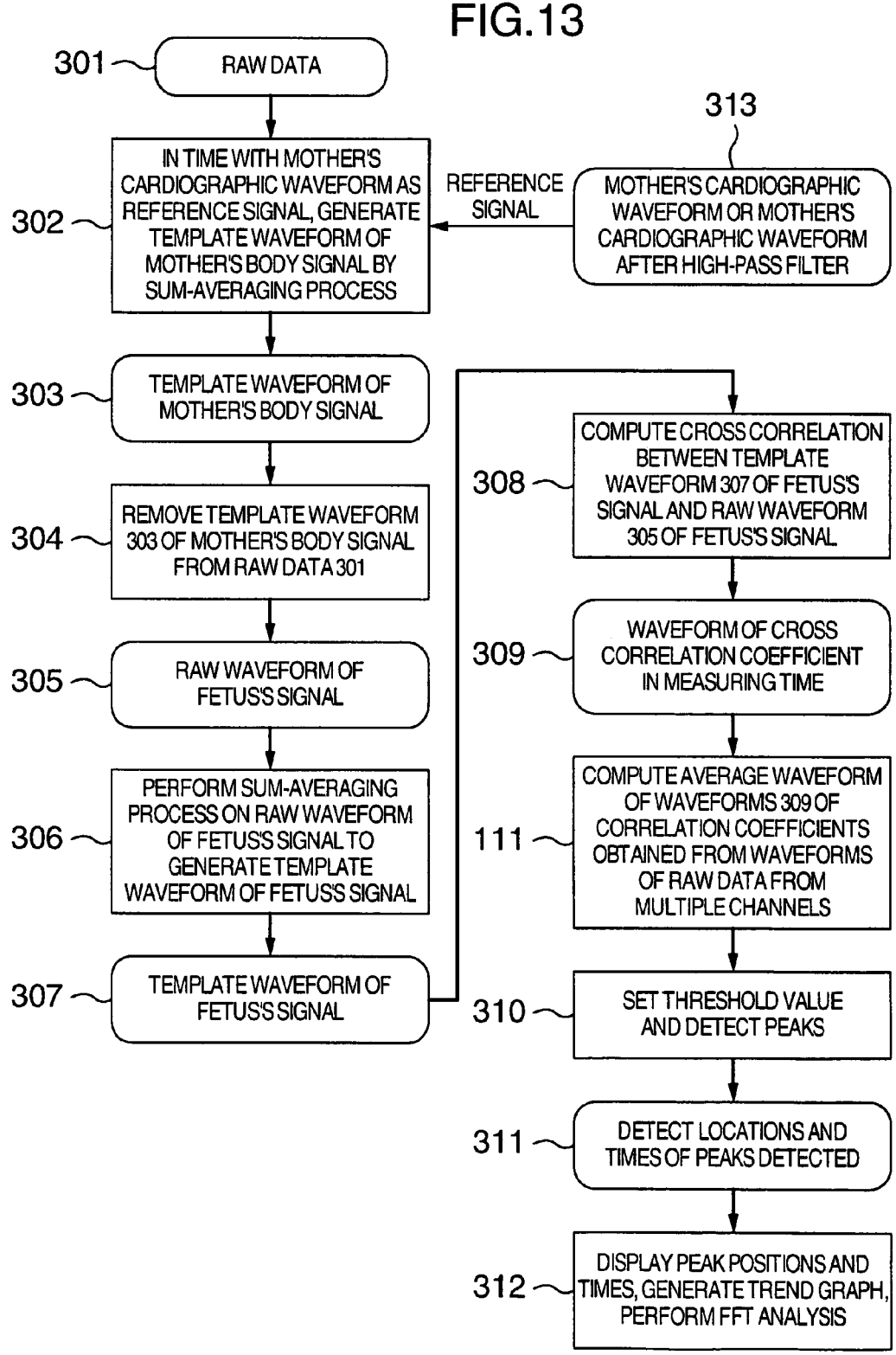
FIG. 13 is a flow diagram showing a procedure for detecting the peaks according to an embodiment of the present invention.

FIG. 13 is a flow diagram showing a procedure for detecting peaks according to an embodiment of the present invention. In the procedure shown in FIG. 6, the waveforms 309 by cross correlation coefficient were obtained by using raw data 301 related to one specified channel; however, in the procedure shown in FIG. 13, the waveforms 309 of cross correlation coefficient is obtained from raw data 301 related to a plurality of channels. In FIG. 13, the processes from 301 to 308 and from 310 to 312 are the same as those shown in FIG. 6. The waveforms 309 of a plurality of cross correlation coefficients in a measuring time, which have been obtained, may be subjected to a sum-averaging process 111, by which waveforms with better S/N ratio can be obtained.

Figure 14:
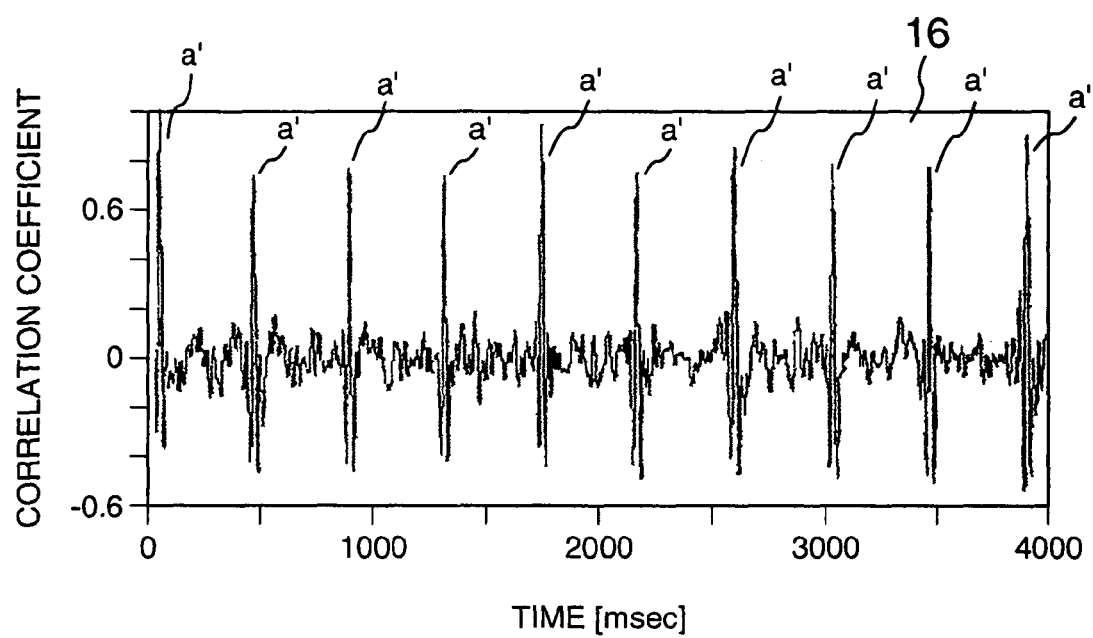
FIG. 14 is a diagram showing waveforms of the average of cross correlation coefficient obtained from waveforms of cross correlation coefficients acquired from a plurality of channels.

FIG. 14 is a diagram showing waveforms of the average of cross correlation coefficient obtained from waveforms of cross correlation coefficients acquired by a plurality of channels in an embodiment of the present invention. More specifically, FIG. 14 presents average waveforms 16 by five correlation coefficients out of the correlation coefficients obtained by the process 111 shown in FIG. 13. It is obvious from the average waveforms 16 that the waveforms a' of the average of cross correlation coefficient derived from waveforms generated by the fetal heart have better S/N ratio than the waveforms a' obtained by one channel as shown in FIG. 11.

By computing average waveforms of cross correlation coefficients of a plurality of channels shown in FIGS. 13 and 14, even when the amplitude of the waveforms generated by the fetal heart is small, it is possible to detect peak times in the fetal heart beats with favorable S/N ratio.

When the amplitude of the magnetic field generated by the maternal heart is smaller than that of the magnetic field generated by the fetal heart, needless to say, the procedures shown in FIGS. 2 to 5 (the process 303 shown in FIGS. 6 and 13) are not performed, and it is only necessary to carry out the processes from 305 to 312 by using the magnetic fields generated by the fetal heart directly from the raw data 301.

The times of peak occurrence of QRS waves, p waves, T waves, for example, obtained by those processes are displayed in broken line graphs at R-R intervals in time series, or instantaneous heart rates converted from those peak times are displayed in a broken line graph in time series. It is possible to add a graphic user interface (GUI) function in order that when these graphs are displayed, if the operator notices any discontinuity, the operator may decide that an error occurred in reading the detected peaks and click on the discontinuity, by which magnetic field waveforms are displayed which correspond to the time when the discontinuity occurred. Installing the GUI function greatly enhances work efficiency.

According to a biomagentic field measuring apparatus in the present invention, it is possible to detect the times of peak occurrence in the waveforms, such as P waves, QRS waves, T waves, with high precision. Moreover, the automatic signal process function improves the detection rate of the peaks and enables R-R analysis of a fetus to be conducted with high efficiency.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A biomagnetic field measuring apparatus comprising:
means for shielding external magnetic fields:
a bed for supporting a pregnant female;
at least one SQUID magnetometer for detecting a biomagnetic field generated by the pregnant female;
a cryostat for keeping the at least one SQUID magnetometer at a low temperature:
a drive circuit for driving the at least one SQUID magnetometer;
a processing unit for collecting output signals of the drive circuit and processing the output signals; and
a display unit for displaying results of the processing,
wherein the processing unit performs (1) a process for obtaining a waveform of a fetal heart by removing a magnetic field waveform generated by a heart of the pregnant female from a biomagnetic field waveform measured of the pregnant female, (2) a process for obtaining a first template waveform of the waveform of the fetal heart, (3) a process for obtaining a waveform of a cross correlation coefficient between the waveform of the fetal heart and the first template waveform, and (4) a process for detecting peaks from the waveform of the cross correlation coefficient, and wherein timings at which detected peaks occur are displayed on the display unit.

2. A biomagnetic field measuring apparatus according to claim 1, wherein the process (1) includes a process for obtaining a second template waveform of the magnetic field waveform generated by the heart of the pregnant female, a baseline correcting process for zeroing the values at an initial point and an end point of the second template waveform, and a process for removing the second template waveform, on which the baseline correcting process has been performed, from the measured biomagnetic field waveform.

3. A biomagnetic field measuring apparatus according to claim 2, wherein the process (1) is performed by using as a reference signal the pregnant female's electrocardiographic waveform measured concurrently with the detection of the biomagnetic field waveform.

4. A biomagnetic field measuring apparatus according to claim 1, wherein in the process (2), the first template waveform is obtained by a sum-averaging process.

5. A biomagnetic field measuring apparatus according to claim 2, wherein the second template waveform is obtained by a sum-averaging process.

6. A biomagnetic field measuring apparatus according to claim 1, further comprising a plurality of SQUID magnetometers and wherein the process (3) includes a process for obtaining waveforms of the cross correlation coefficients from waveforms of the biomagnetic fields measured by each SQUID magnetometer of the plurality of SQUID magnetometers and a process for obtaining an average waveform of the waveforms of the plurality of cross correlatlon coefficients obtained, and wherein the average waveform is used as the waveform of the cross correlation coefficients.

* * * * *